United States Patent [19]
Hattersley et al.

[11] Patent Number: 5,846,931
[45] Date of Patent: Dec. 8, 1998

[54] COMPOSITIONS COMPRISING BONE MORPHOGENIC PROTEINS AND TRUNCATED PARATHYROID HORMONE RELATED PEPTIDE AND METHODS OF INDUCING CARTILAGE BY ADMINISTRATION OF SAME

[76] Inventors: Gary Hattersley, 10 Rogers St., #303, Cambridge, Mass. 02142; Vicki A. Rosen, 2 Cedar Rd., Chestnut Hill, Mass. 02167

[21] Appl. No.: 926,942

[22] Filed: Sep. 10, 1997

Related U.S. Application Data

[63] Continuation of Ser. No. 622,101, Mar. 26, 1996, Pat. No. 5,700,774.

[51] Int. Cl.⁶ .................. C07K 14/495; C07K 14/51; C07K 14/635; A61K 38/17
[52] U.S. Cl. .................... 514/2; 514/8; 514/12; 424/85.1; 530/350; 530/351; 530/397; 530/399; 530/300; 530/324
[58] Field of Search ................ 530/350, 351, 530/397, 399, 300, 324; 424/85.1; 514/2, 8, 12

[56] References Cited

U.S. PATENT DOCUMENTS

| | | | |
|---|---|---|---|
| 5,013,649 | 5/1991 | Wang et al. | 435/69.1 |
| 5,106,748 | 4/1992 | Wozney et al. | 435/252.3 |
| 5,108,922 | 4/1992 | Wang et al. | 435/365.1 |
| 5,116,738 | 5/1992 | Wang et al. | 435/69.1 |
| 5,141,905 | 8/1992 | Rosen et al. | 435/69.1 |
| 5,187,076 | 2/1993 | Wozney et al. | 435/69.1 |
| 5,455,329 | 10/1995 | Wingender | 530/324 |
| 5,457,047 | 10/1995 | Wingender | 435/252.3 |
| 5,457,092 | 10/1995 | Schluter | 514/12 |

FOREIGN PATENT DOCUMENTS

| | | |
|---|---|---|
| WO 91/18098 | 11/1991 | WIPO. |
| WO 93/00050 | 1/1993 | WIPO. |
| WO 93/00432 | 1/1993 | WIPO. |
| WO 93/09229 | 5/1993 | WIPO. |
| WO 93/16099 | 8/1993 | WIPO. |
| WO 94/01557 | 1/1994 | WIPO. |
| WO 94/15949 | 7/1994 | WIPO. |
| WO 94/15965 | 7/1994 | WIPO. |
| WO 94/15966 | 7/1994 | WIPO. |
| WO 94/21681 | 9/1994 | WIPO. |
| WO 94/26892 | 11/1994 | WIPO. |
| WO 94/26893 | 11/1994 | WIPO. |
| WO 95/01801 | 1/1995 | WIPO. |
| WO 95/01802 | 1/1995 | WIPO. |
| WO 95/16035 | 6/1995 | WIPO. |

OTHER PUBLICATIONS

Toriumi et al., Arch Otolaryngol Head Neck Surg 117:1101–1112 (1991).
Wozney, "Bone Morphogenetic Proteins and Their Gene Expression" in *Cellular and Molecular Biology of Bone* pp. 131–167 (Academic Press, Inc.)(1993).
Karaplis et al., Genes & Development 8:277–289 (1994).
Tsukazaki et al., Calcif Tissue Int 57:196–200 (1995).
Sporn et al., Science 233:532–534 (1986).
Weeks and Melton, Cell 51:861–867 (1987).
Padgett et al., Nature (London) 325:81–84 (1987).
Doctor et al., Dev Biol 151:591–505 (1992).
Karaplis et al., Mol Endocrin 4:441–446.
Mangin et al., PNAS 85:597–601 (1988).
Mangin et al., Gene 95:195–202 (1990).
Martin et al., Crit Rev Biochem Mol Biol 26:377–395 (1991).
Amizuka et al., J Cell Biol 126:1611–1623 (1994).

*Primary Examiner*—Elizabeth Kemmerer
*Attorney, Agent, or Firm*—Steven R. Lazar

[57] ABSTRACT

Compositions of proteins with chondrocyte and cartilaginous tissue inducing activity, as well as method of using those compositions, are disclosed. The compositions comprise one or more proteins of the transforming growth factor-β (TGF-β) superfamily of proteins, particularly bone morphogenetic proteins (BMPs), in combination with parathyroid hormone related polypeptide (PTHrP) or an equivalent PTH-like polypeptide. The compositions and methods are useful in the treatment of osteoarthritis, cartilage defects and in related tissue repair.

7 Claims, No Drawings

COMPOSITIONS COMPRISING BONE MORPHOGENIC PROTEINS AND TRUNCATED PARATHYROID HORMONE RELATED PEPTIDE AND METHODS OF INDUCING CARTILAGE BY ADMINISTRATION OF SAME

This application is a continuation of application Ser. No. 08/622,101, filed Mar. 26, 1996, now U.S. Pat. No. 5,700,774.

FIELD OF THE INVENTION

The present invention relates to novel methods and compositions for repairing, reducing or preventing damage to cartilage and cartilaginous tissue. The methods and compositions may further be useful for the induction and maintenance of cartilaginous tissue formation, wound healing and cartilage and other tissue repair. These methods and compositions may also be useful for augmenting the activity of bone morphogenetic proteins. In particular, the present application relates to the use of compositions comprising an osteogenic or cartilage-inducing member of the transforming factor beta [TGF-β] superfamily of proteins, such as a bone morphogenetic protein [BMP], in combination with parathyroid hormone-related peptide [PTHrP]. The compositions are useful for induction and maintenance of cartilaginous tissue, such as articular cartilage.

BACKGROUND OF THE INVENTION

The search for the molecule or molecules responsible for formation of bone, cartilage, tendon and other tissues present in bone and other tissue extracts has led to the discovery of a novel set of molecules called the Bone Morphogenetic Proteins (BMPs). The structures of several proteins, designated BMP-1 through BMP-15, have previously been elucidated. The unique inductive activities of these proteins, along with their presence in bone, cartilage and/or other vital tissues, suggests that they are important regulators of bone and other tissue repair processes, and may be involved in tissue formation, maintenance and repair. There is a need to identify improved methods and compositions for formation, maintenance and repair of such tissues.

Members of the bone morphogenetic protein family have been shown to be useful for induction of cartilage and bone formation. For example, BMP-2 has been shown to be able to induce the formation of new cartilage and/or bone tissue in vivo in a rat ectopic implant model, see U.S. Pat. No. 5,013,649; in mandibular defects in dogs, see Toriumi et al., *Arch. Otolaryngol Head Neck Surg.*, 117:1101–1112 (1991); in femoral segmental defects in sheep, see Gerhart et al., *Trans Orthop Res Soc*, 16:172 (1991). Other members of the BMP family have also been shown to have osteogenic activity, including BMP-4, -6 and -7, see Wozney, *Bone Morphogenetic Proteins and Their Gene Expression*, in *Cellular and Molecular Biology of Bone*, pp. 131–167 (Academic Press, Inc. 1993). BMP proteins have also been shown to demonstrate inductive and/or differentiation potentiating activity on a variety of other tissues, including cartilage, tendon, ligament, neural tissue.

Parathyroid hormone-related peptide (PTHrP) is a protein which is known exist in at least three isoforms of 139, 141 and 173 amino acids. [Karaplis et al., *Genes & Development*, 8:277–289 (1994). PTHrP is highly homologous to the N-terminal fragment of parathyroid hormone (PTH), and binds the same receptor as PTH. PTHrP appears to play a substantial role in calcium metabolism by an autocrine/paracrine mechanism, and also appears to regulate embryonal development, vascular tone and nutrition. Tsukazaki et al., *Calcif Tissue Int* 57:196–200 (1995). It has recently been shown that mice deficient in PTHrP exhibit abnormal cartilage maturation, indicating that PTHrP is an essential factor for chondrocyte development and maturation. In Tsukazaki, it is reported that PTHrP expression in articular cartilage varies in intensity and localization during development, while the PTH/PTHrP receptor is highly expressed in the growth plate and in articular cartilage.

SUMMARY OF THE INVENTION

The present invention relates to compositions useful for inducing cartilaginous tissue formation in a patient in need of same, said compositions comprising one or more protein members of the transforming growth factor-β (TGF-β) superfamily together with parathyroid hormone related peptide (PTHrP), or an equivalent PTH-like polypeptide. Preferably the compositions of the invention comprise at least one protein member of the bone morphogenetic protein (BMP) family and parathyroid hormone related peptide (PTHrP). In particular preferred embodiments, the composition comprises a bone morphogenetic protein is selected from the group consisting of BMP-2, BMP-4, BMP-5, BMP-7, BMP-12 and BMP-13 together with PTHrP or an equivalent PTH-like polypeptide. In the most preferred embodiments, the compositions comprise BMP-2, BMP-13, heterodimers of BMP-2 and BMP-13 or combinations of the above, and PTHrP or an equivalent PTH-like polypeptide; especially preferred BMPs are BMP-2 and BMP-13. The compositions may further comprise one or more additional members of the BMP subfamily of proteins. In preferred embodiments of the invention, the PTHrP used is PTHrP1–34, a truncated peptide comprising the first 34 amino acids of the N-terminal portion of PTH. In preferred embodiments of the invention, the compositions comprise BMP-2 and one or more additional proteins selected from the group consisting of BMP-4, BMP-5, BMP-7, BMP-12 and BMP-13; or BMP-13 and one or more additional proteins selected from the group consisting of BMP-2, BMP-4, BMP-5, BMP-7 and BMP-12 together with PTHrP1–34, PTHrP or another PTH-like polypeptide.

In other embodiments, the present invention relates to methods for inducing the formation and maintenance of cartilage in a patient, for example a patient suffering from arthritis, particularly osteoarthritis, or a patient with an articular cartilage defect or other cartilaginous tissue defect, said method comprising administering to said patient an effective amount of the above compositions. In a particular embodiment, the method of the present invention relates to a method for treating articular cartilage defects or damage in a patient in need of same, said method comprising administering to said patient an effective amount of the above compositions. The invention further relates to methods for inducing the formation of cartilage and cartilaginous tissue comprising administering to a patient a composition comprising a member of the TGF-β superfamily of proteins and Parathyroid hormone-related peptide (PTHrP).

The methods and compositions of the present invention are thus useful for repairing, reducing or preventing damage to cartilage and cartilaginous tissue. The methods and compositions may further be useful for the induction and maintenance of cartilaginous tissue formation, wound healing and cartilage and other tissue repair. for the induction of cartilaginous tissue, such as articular cartilage, the meniscus, and the articular surfaces of developing bone, or for the treatment of diseases or defects of cartilaginous tissue, such as arthritis, particularly osteoarthritis.

DETAILED DESCRIPTION OF THE INVENTION

The methods and compositions of the present invention comprise a combination of one or more proteins from the transforming growth factor-β superfamily with one or more parathyroid hormone-related peptides. The transforming growth factor-β superfamily is a well-characterized family of proteins involved in cellular proliferation and differentiation of cells into various tissues. Members of the TGF-β superfamily are generally dimeric in structure, comprising two monomeric units which are produced by proteolytic cleavage from a larger precursor protein, of which the processed monomer represents the carboxyl terminal portion. The dimeric TGF-β proteins generally have molecular weights of approximately 20,000 to 35,000 and share a common cysteine pattern in the mature protein region. See, for example, Sporn et al., *Science*, 233:532–534 (1986) and the papers cited therein. The TGF-β superfamily includes several subgroups beside TGF-β1 through -β5, are the bone morphogenetic proteins (BMPs), growth and differentiation factors (GDFs), the inhibins, as well as GDNF and Mullerian inhibitory substance and other structurally related proteins. The TGF-β superfamily also includes proteins from other species, which have been characterized and are highly conserved compared to the mammalian TGF-βs, including Vg1 (Xenopus), see for example, Weeks and Melton, *Cell*, 51:861–867 (1987); Dpp, Screw and 60A (Drosophila), see for example Padgett et al., *Nature (London)*, 325:81–84 (1987); Doctor et al., *Dev. Biol.* 151:591–505 (1992); and more recently identified proteins including Univin (sea urchin), Dorsalin-1 (chicken) and Radar (Zebrafish). Other factors which may be effectively used in the composition include synthetic molecules or fragments of a TGF-β superfamily member which are able to bind to a TGF-β receptor molecule.

Methods for production of numerous members of the TGF-β superfamily useful in the present invention are known and/or described in the literature. For example, the structure and methods for production of many BMPs, including BMP-2, BMP-3, BMP-4, BMP-5, BMP-6 and BMP-7, are disclosed, for instance, in U.S. Pat. Nos. 5,108,922; 5,013,649; 5,116,738; 5,106,748; 5,187,076; and 5,141,905; BMP-8, disclosed in PCT publication WO91/18098; BMP-9, disclosed in PCT publication WO93/00432; BMP-10, disclosed in PCT application WO94/26893; BMP-11, disclosed in PCT application WO94/26892; BMP-12 and BMP-13, disclosed in PCT application WO 95/16035, or BMP-15, disclosed in co-pending patent application, Ser. No. 08/446,924, filed on May 18, 1995. The structure of Vgr-2, and the growth and differentiation factors [GDFs], including those described in PCT applications WO94/15965; WO94/15949; WO95/01801; WO95/01802; WO94/21681; WO94/15966; and others are also known. Other TGF-β proteins which may be useful in the present invention include BIP, disclosed in WO94/01557; and MP52, disclosed in PCT application WO93/16099. Methods for production of heterodimeric proteins comprising two distinct monomeric units, each comprising the amino acid sequence of one of the above TGF-β proteins, are described in WO93/09229. The disclosures of all of the above applications are hereby incorporated by reference.

Parathyroid hormone-related peptide (PTHrP) is closely related in structure to parathyroid hormone. PTHrP is known to exist in at least three isoforms of 139, 141 and 173 amino acids. [Karaplis et al., *Genes & Development*, 8:277–289 (1994). PTHrP is highly homologous to the N-terminal fragment of parathyroid hormone (PTH), and binds the same receptor as PTH. The nucleotide and amino acid sequences of the PTHrP gene from rat, mouse and human are known and may be used to produce PTHrP-like polypeptides useful in the present invention. [See Karaplis et al., *Mol. Endocrin.* 4:441–446 [1990][rat]; Mangin et al., *PNAS* 85:597–601 (1988)[human] and Mangin et al., *Gene* 95:195–202 (1990) [mouse]; and Martin et al., *Crit Rev Biochem Mal Biol* 26:377–395 (1991).] In a preferred embodiment of the present invention, a variant of PTHrP is used in which one or more amino acids from the carboxy terminus has been deleted. For example, PTHrP1–34, which comprises the first 34 amino acids of PTHrP, is used in one preferred embodiment of the present invention. Also useful in the present invention are PTH-like polypeptides which are equivalent to PTHrP1–34 in their ability to enhance survival of chondrocytes. Such PTH-like polypeptides may include, for example, PTH, whether of human, porcine, bovine or other mammalian origin; variants of PTH, such as those described in Wingender et al., U.S. Pat. No. 5,455,329; Wingender et al., U.S. Pat. No. 5,457,047; and Schluter et al., U.S. Pat. No. 5,457,092, and the references cited therein; as well as variants of the above in which one or more amino acids of PTH has been deleted from the carboxy and/or amino terminal portions of the molecule. The disclosures of the above publications are hereby incorporated by reference. PTH, PTHrP and the above variants may be produced via recombinant DNA engineering using the known sequences of the PTH and PTHrP proteins, or may be isolated by purification.

The methods and compositions of the present invention may comprise simultaneous or sequential administration of at least two active agents, a TGF-β protein and a parathyroid hormone-related peptide, to a patient or site in need of cartilage repair, formation or maintenance. For sequential administration, one or both of the active agents may be encapsulated or otherwise maintained in contact with a carrier which provides for slow release of the agent. The methods and compositions may comprise the active agents in a weight ratio of from about 90:10, to about 10:90. Preferably the active agents are present in a weight ratio of about 70:30 to 30:70. Most preferred are methods and compositions comprising the active agents in a weight ratio of about 50:50.

The compositions of the invention may comprise, in addition to a TGF-β protein and a parathyroid hormone-related peptide, other therapeutically useful agents including growth factors such as epidermal growth factor (EGF), transforming growth factor-α, activins, inhibins, platelet derived growth factor (PDGF), fibroblast growth factor (FGF), and fibroblast growth factor-4 (FGF-4), parathyroid hormone (PTH), leukemia inhibitory factor (LIF/HILDA/DIA), and insulin-like growth factors (IGF-I and IGF-II). Portions of these agents may also be used in compositions of the present invention. The compositions may also include an appropriate matrix for instance, for supporting the composition and providing a surface for cartilage or for other connective tissue growth. The matrix may provide slow release of the protein and/or the appropriate environment for presentation thereof.

The methods and compositions of the present invention employ proteins which are able to induce cartilaginous tissue or other tissue formation in circumstances where such tissue is not normally formed, and has application in the healing of cartilage, for example articular cartilage tears, deformities and other cartilage defects in humans and other animals. Such methods and compositions employing cartilaginous tissue inducing proteins may have prophylactic use in preventing damage to cartilaginous tissue, as well as use in the improved fixation of cartilage to bone or other tissues, and in repairing defects to cartilage tissue. De novo cartilaginous tissue formation induced by a composition of the present invention contributes to the repair of congenital, trauma induced, or other cartilage defects of other origin, and is also useful in surgery for attachment or repair of cartilage. The methods and compositions of the invention may also be useful in the treatment of arthritis and other cartilage defects. The methods and compositions of the present invention can also be used in other indications wherein it is desirable to heal or regenerate cartilage tissue. Such indications include, without limitation, regeneration or repair of injuries to the articular cartilage. The methods and compositions of the present invention may provide an environment to attract cartilage-forming cells, stimulate growth of cartilage-forming cells or induce differentiation of progenitors of cartilage-forming cells and chondrocytes.

The compositions and methods of the present invention may also be useful for treating cell populations, such as embryonic cells or stem cell populations, to enhance or enrich the growth, survival and/or differentiation of the cells into chondrocytes or other cell types. In another embodiment, the compositions and methods of the present invention may be used to treat chondrocytic cell lines, such as articular chondrocytes, in order to maintain chondrocytic phenotype and survival of the cells. The treated cell populations may be useful for gene therapy applications.

The proteins useful in the methods of the present invention are useful for inducing the formation, maintenance and survival of chondrocytes and/or cartilaginous tissue. It is contemplated that these proteins may have the ability to induce the formation of other types of tissue, such as tendon and ligament, as well. The cartilaginous tissue-inducing methods and compositions provided herein also may include factors encoded by the sequences similar to those of naturally-occurring TGF-β proteins, into which modifications are naturally provided (e.g. allelic variations in the nucleotide sequence which may result in amino acid changes in the polypeptide) or deliberately engineered. For example, synthetic polypeptides may wholly or partially duplicate continuous sequences of the amino acid residues of BMP-2 or BMP-13. These sequences, by virtue of sharing primary, secondary, or tertiary structural and conformational characteristics with cartilaginous tissue growth factor polypeptides of naturally-occurring BMP-2 or BMP-13 may possess cartilaginous or other tissue growth factor biological properties in common therewith. Thus, they may be employed as biologically active substitutes for naturally-occurring cartilaginous tissue inducing polypeptides in therapeutic methods and compositions.

The proteins useful in the present invention, or the DNA sequences encoding therefor, may be engineered to provide one or more additional cysteine residues to increase potential dimer formation, particularly for forming dimers of the TGF-β proteins. The resulting DNA sequence would be capable of producing a "cysteine added variant" of the protein. Production of "cysteine added variants" of proteins is described in U.S. Pat. No. 5,166,322, the disclosure of which is hereby incorporated by reference. Other specific mutations of the sequences of cartilaginous tissue inducing proteins described herein involve modifications of glycosylation sites. These modifications may involve O-linked or N-linked glycosylation sites. For instance, the absence of glycosylation or only partial glycosylation results from amino acid substitution or deletion at asparagine-linked glycosylation recognition sites. The asparagine-linked glycosylation recognition sites comprise tripeptide sequences which are specifically recognized by appropriate cellular glycosylation enzymes. These tripeptide sequences may be asparagine-X-threonine, asparagine-X-serine or asparagine-X-cysteine, where X is usually any amino acid except proline. A variety of amino acid substitutions or deletions at one or both of the first or third amino acid positions of a glycosylation recognition site (and/or amino acid deletion at the second position) results in non-glycosylation at the modified tripeptide sequence. Additionally, bacterial expression of protein will also result in production of a non-glycosylated protein, even if the glycosylation sites are left unmodified.

The methods of the present invention for inducing cartilaginous tissue formation may comprise administering to a patient an effective amount of a composition comprising one or more protein members of the transforming growth factor-β (TGF-β) superfamily together with parathyroid hormone related peptide (PTHrP), or an equivalent PTH-like polypeptide. Alternatively, the methods of the present invention for inducing cartilaginous tissue formation may comprise heterodimers comprised of two distinct monomeric units, each of which has the amino acid sequence of a member of the TGF-β superfamily, together with PTHrP, or an equivalent PTH-like polypeptide. Preferably, the compositions of the invention comprise one or more members of the bone morphogenetic protein (BMP) family, together with PTHrP or an equivalent PTH-like polypeptide. In particular preferred embodiments, the composition comprises a bone morphogenetic protein selected from the group consisting of BMP-2, BMP-4, BMP-5, BMP-7, BMP-12 and BMP-13, or heterodimers of the above, together with PTHrP or an equivalent PTH-like polypeptide. In the most preferred embodiments, the composition comprises BMP-2, BMP-13, heterodimers of BMP-2 and BMP-13 or combinations of the above, and PTHrP or an equivalent PTH-like polypeptide. The above compositions may optionally comprise one or more additional proteins which are members of the TGF-β superfamily, preferably of the BMP family of proteins. In preferred embodiments, the composition comprises BMP-2 and one or more additional proteins selected from the group consisting of BMP-4, BMP-5, BMP-7, BMP-12, BMP-13 and heterodimers of the above; or BMP-13 and one or more additional proteins selected from the group consisting of BMP-2, BMP-4, BMP-5, BMP-7, BMP-12 and heterodimers of the above; each together with PTHrP or an equivalent PTH-like polypeptide. As discussed above, these compositions may be used to induce the formation, maintenance and survival of chondrocytes and/or cartilaginous tissue or other tissue. It is contemplated that such compositions may also be used for articular cartilage repair, wound healing and other tissue repair, such as skin repair. It is further contemplated that proteins of the invention may increase neuronal survival and therefore be useful in transplantation and treatment of conditions exhibiting a decrease in neuronal survival. Compositions and methods of the invention may further be useful for induction and repair of other tissue, including wound healing.

In a preferred embodiment of the present invention, more than one protein of the TGF-β superfamily may be used together with PTHrP to enhance the induction, maintenance and differentiation of one or more cell and/or tissue types, including cartilaginous tissue. For example, a composition comprising both BMP-2 and BMP-13 implanted together with PTHrP may give rise to both bone and cartilaginous tissue. Such a composition may be useful for treating defects of the junction between cartilage and bone, causing cartilage and bone to form simultaneously at contiguous anatomical locations, and may therefore be useful for regenerating tissue at the site of cartilage attachment to bone.

It is contemplated that the methods and compositions of the invention may also be useful in wound healing, such as skin healing and related tissue repair. The types of wounds include, but are not limited to burns, incisions and ulcers. (See, e.g. PCT Publication WO84/01106 for discussion of wound healing and related tissue repair).

The methods and compositions of the invention further comprise heteromolecules comprised of different TGF-β moieties, in combination with PTHrP or an equivalent PTH-like polypeptide. Preferably, the heteromolecule is a heterodimer, for example, of two monomers each comprising the amino acid sequence of a BMP protein. For example, a method and composition of the invention may comprise a disulfide linked dimer comprising a BMP-2 protein subunit and a subunit from one of the other BMP proteins described above. Thus, in a particular embodiment, the present invention comprises compositions and methods employing a heterodimer wherein one subunit comprises the amino acid sequence of BMP-2, and one subunit comprises an amino acid sequence for a bone morphogenetic protein selected from the group consisting of BMP-3, BMP-4, BMP-5, BMP-6, BMP-7, BMP-8, BMP-9. BMP-10, BMP-11, BMP-12, BMP-13 or BMP-15. Further embodiments may comprise a heterodimer of other disulfide bonded TGF-β moieties, including VGR-2, MP52, MIS, activin and TGF-β. For example, the heterodimer may comprise one subunit comprising the amino acid sequence of BMP-2 or BMP-13, and the other subunit may comprise the amino acid of activin. Further, compositions of the present invention may be combined with other agents beneficial to the treatment of the defect, wound, or tissue in question.

It is expected that the compositions and methods of the invention may act in concert with or perhaps synergistically with administration of other related proteins and growth factors. Further therapeutic methods and compositions of the invention therefore comprise a therapeutic amount of at least one of the BMP proteins, whether homodimeric or heterodimeric, in combination with PTHrP or an equivalent PTH-like polypeptide, and other growth factors.

The preparation and formulation of such physiologically acceptable protein compositions, having due regard to pH, isotonicity, stability and the like, is within the skill of the art. The therapeutic compositions are also presently valuable for veterinary applications due to the lack of species specificity in TGF-β proteins. Particularly domestic animals and thoroughbred horses in addition to humans are desired patients for such treatment with the compositions of the present invention.

The therapeutic method includes administering the composition topically, systemically, or locally as an injectable and/or implant or device. When administered, the therapeutic composition for use in this invention is, of course, in a pyrogen-free, physiologically acceptable form. Further, the composition may desirably be encapsulated or injected in a viscous form for delivery to the site of tissue damage. Topical administration may be suitable for wound healing and tissue repair. Therapeutically useful agents other than the proteins which may also optionally be included in the composition as described above, may alternatively or additionally, be administered simultaneously or sequentially with the composition in the methods of the invention. In addition, the compositions of the present invention may be used in conjunction with presently available treatments for cartilage injuries, such as suture (e.g., vicryl sutures or surgical gut sutures, Ethicon Inc., Somerville, N.J.) or cartilage allograft or autograft, in order to enhance or accelerate the healing potential of the suture or graft. For example, the suture, allograft or autograft may be soaked in the compositions of the present invention prior to implantation. It may also be possible to incorporate the protein or composition of the invention onto suture materials, for example, by freeze-drying.

The compositions of the present invention may include an appropriate matrix and/or sequestering agent as a carrier. For instance, the matrix may support the composition or provide a surface for cartilaginous tissue formation and/or other tissue formation. The matrix may provide slow release of the protein and/or the appropriate environment for presentation thereof. The sequestering agent may be a substance which aids in ease of administration through injection or other means, or may slow the migration of protein from the site of application.

The choice of a carrier material is based on biocompatibility, biodegradability, mechanical properties, cosmetic appearance and interface properties. The particular application of the compositions will define the appropriate formulation. Potential matrices for the compositions may be biodegradable and chemically defined. Further matrices are comprised of pure proteins or extracellular matrix components. Other potential matrices are nonbiodegradable and chemically defined. Preferred matrices include collagen-based materials, including sponges, such as Helistat' (Integra LifeSciences, Plainsboro, N.J.), or collagen in an injectable form, as well as sequestering agents, which may be biodegradable, for example hyaluronic acid derived. Biodegradable materials, such as cellulose films, or surgical meshes, may also serve as matrices. Such materials could be sutured into an injury site, or wrapped around the cartilage.

Another preferred class of carrier are polymeric matrices, including polymers of poly(lactic acid), poly(glycolic acid) and copolymers of lactic acid and glycolic acid. These matrices may be in the form of a sponge, or in the form of porous particles, and may also include a sequestering agent. Suitable polymer matrices are described, for example, in WO93/00050, the disclosure of which is incorporated herein by reference.

Preferred families of sequestering agents include blood, fibrin clot and/or cellulosic materials such as alkylcelluloses (including hydroxyalkylcelluloses), including methylcellulose, ethylcellulose, hydroxyethylcellulose, hydroxypropylcellulose, hydroxypropyl-methylcellulose, and carboxymethylcellulose, the most preferred being cationic salts of carboxymethylcellulose (CMC). Other preferred sequestering agents include hyaluronic acid, sodium alginate, poly(ethylene glycol), polyoxyethylene oxide, carboxyvinyl polymer and poly(vinyl alcohol). The amount of sequestering agent useful herein is 0.5–20 wt %, preferably 1–10 wt % based on total formulation weight, which represents the amount necessary to prevent desorbtion of the protein from the polymer matrix and to provide appropriate handling of the composition, yet not so much that the progenitor cells are prevented from infiltrating the matrix, thereby providing the protein the opportunity to assist the activity of the progenitor cells.

Additional optional components useful in the practice of the subject application include, e.g. cryogenic protectors such as mannitol, sucrose, lactose, glucose, or glycine (to protect the protein from degradation during lyophilization), antimicrobial preservatives such as methyl and propyl parabens and benzyl alcohol; antioxidants such as EDTA, citrate and BHT (butylated hydroxytoluene); and surfactants such as poly(sorbates) and poly(oxyethylenes); etc.

As described above, the compositions of the invention may be employed in methods for treating a number of cartilage defects, such as the regeneration of cartilaginous tissue in areas of cartilage damage, to assist in repair of tears of cartilage tissue, and various other types of tissue defects or wounds. These methods, according to the invention, entail administering to a patient needing such cartilaginous tissue or other tissue repair, a composition comprising an effective amount of an osteogenic or cartilage-inducing member of the transforming factor beta [TGF-β] superfamily of proteins, such as a bone morphogenetic protein [BMP], preferably BMP-2, BMP-4, BMP-5, BMP-7, BMP-12 and BMP-13, in combination with parathyroid hormone-related peptide [PTHrP] or an equivalent PTH-like polypeptide.

In another embodiment, the methods may entail administration of a heterodimeric protein in which each of the monomers comprises the amino acid sequence of an osteogenic or cartilage-inducing member of the TGFβ superfamily of proteins, such as a BMP, particularly, BMP-2, BMP-4, BMP-5, BMP-7, BMP-12 and BMP-13, in combination with PTHrP or an equivalent PTHrP-like polypeptide. In a preferred embodiment, each of the monomers is selected from the group consisting of BMP-2, BMP-4, BMP-5, BMP-7, BMP-12 and BMP-13.

Thus, a further aspect of the invention is a therapeutic method and composition for inducing or maintaining chondrocytes or cartilaginous tissue, for repairing cartilaginous tissue, for repairing cartilage as well as treating arthritis and other conditions related to arthritis or cartilage defects. Such compositions comprise a therapeutically effective amount of one or more osteogenic or cartilaginous tissue inducing proteins, such as BMP-2 or BMP-13, in combination with PTHrP or an equivalent PTH-like polypeptide, in admixture with a pharmaceutically acceptable vehicle, carrier or matrix.

The dosage regimen will be determined by the attending physician considering various factors which modify the action of the composition, e.g., amount of cartilaginous tissue desired to be formed the site of cartilaginous tissue damage, the condition of the damaged cartilaginous tissue, the size of a wound, type of damaged tissue, the patient's age, sex, and diet, the severity of any infection, time of administration and other clinical factors. The dosage may vary with the type of matrix used in the reconstitution and the types of additional proteins in the composition. The addition of other known growth factors, such as IGF-I (insulin like growth factor I), to the final composition, may also affect the dosage.

Progress can be monitored by periodic assessment of chondrocyte survival, cartilaginous tissue formation, or cartilaginous tissue growth and/or repair. The progress can be monitored by methods known in the art, for example, X-rays, arthroscopy, histomorphometric determinations and tetracycline labeling.

The following examples illustrate practice of the present invention in using the compositions and methods described above. The methods are useful for producing, recovering and maintaining chondrocytes and/or human cartilaginous tissue inducing protein, employing the methods and compositions of cartilaginous tissue inducing proteins and PTHrP and equivalent PTH-like polypeptides. Although the examples demonstrate the invention with respect to BMP-2 and PTHrP1–34, with minor modifications within the skill of the art, the same results may be attainable with other TGF-β proteins, particularly other BMPs, as well as equivalent PTH-like polypeptides.

EXAMPLES

1. Effect of Combination of BMP and PTHrP on Expression and Maintenance of Cartilage Specific mRNA.

PTHrP was tested for its effect on cell lines derived from E13 mouse limb buds either alone or in combination with BMP-2. Cells were grown to confluence in DME medium supplemented with 10% fetal calf serum (FCS). At confluence, cells were transferred to DME medium supplemented with 1% FCS and cultured for 1, 2, 4 or 8 days in the presence of either BMP-2 (100 ng/ml), PTHrP1–34 (100 ng/ml)(Peninsular Laboratories Inc). or a combination of BMP-2 and PTHrP1–34. Northern analysis was used to determine expression of tissue specific mRNAs for cartilage (proteoglycan core protein, collagen type II and decorin), bone (osteocalcin, alkaline phosphatase and collagen type I) and hypertrophic cartilage (collagen type X). Treatment of limb bud cells with a combination of BMP-2 and PTHrP1–34 induced and maintained expression of proteoglycan core protein and collagen type II. Expression of osteocalcin, collagen type I, alkaline phosphatase and collagen type X were all strongly inhibited by treatment with the combination of BMP-2 and PTHrP1–34, compared with treatment with BMP-2 alone. PTHrP1–34 alone did not induce expression of any of these RNAs.

These observations, combined with the reported localization of PTHrP1–34 in articular cartilage indicate that a combination of BMP-2 and PTHrP1–34 induces the formation and maintenance of cartilaginous tissue, rather than hypertrophic cartilage or bone. This conclusion is supported by the reported localization of PTHrP in articular cartilage and the phenotype of mice containing mutations to the PTHrP1–34 gene.

Example 2: Cartilage Induction Using BMP and PTHrP

Combinations of other BMPs and PTHrP1–34 are tested for their effect on cell lines derived from E13 mouse limb buds as described in Example 1 above. Cells are grown to confluence on medium containing DME supplemented with 1% fetal calf serum. The cells are treated with (a) BMP, such as BMP-13, alone; (b) PTHrP alone; or (c) combinations of BMP and PTHrP; in varying doses from less than 1 ng/ml up to about $5.0 \times 10^3$ ng/ml. After 10 days of treatment, histologic and Northern analyses are performed for expression of cartilage and bone markers as described in Example 1 above.

Example 3: Full Thickness Articular Cartilage Repair Model

A full thickness articular cartilage defect model in the femoral-patellar joint of adult rabbits is used to evaluate the ability of the combination of BMPs and PTHrP to affect cartilage and bone repair. Adult New Zealand White rabbits are anesthetized and prepared for sterile surgery. A 3×3 mm defect through articular cartilage and into underlying subchondral bone is drilled into the patellar groove of the knee joint. The defect is either left empty, filled with collagen sponge (controls), or with collagen sponge soaked with 10 μg rhBMP-2 alone, PTHrP alone, another BMP protein alone, or a combination of BMP and PTHrP (experimental).

The incision is closed and animals are allowed free movement within their cages for 4 weeks. After 4 weeks the animals are humanely euthanatized and the articular cartilage/subchondral bone defect is evaluated histologically for tissue architecture, quantity and quality of repair tissue. Northern analysis is performed for additional phenotyping.

What is claimed is:

1. A composition comprising:
   (a) a member selected from the group consisting of the transforming growth factor-$\beta$ (TGF-$\beta$) superfamily; and
   (b) a truncated parathyroid hormone related peptide (PTHrP) comprising amino acids 1 to 34 of PTHrP; said composition having the activity of inducing the formation or maintenance of cartilaginous tissue in a patient when administered to said patient.

2. The composition of claim 1, wherein its member of (a) is a bone morphogenic protein (BMP) is selected from the group consisting of BMP-1, BMP-3, BMP-6, BMP-8, BMP-9, BMP-10, BMP-11, BMP-14 and BMP-15.

3. The composition of claim 2, wherein said composition further comprises a member selected from the group consisting of the BMP family of proteins.

4. A method for inducing the formation or maintenance of cartilaginous tissue in a patient, comprising administering to the patient an effective amount of the composition of claim 1.

5. A method according to claim 4, wherein the patient is suffering from arthritis.

6. A method according to claim 4, wherein the patient is suffering from an articular cartilage defect or damage.

7. A method for inducing cartilaginous tissue formation, growth, differentiation, proliferation, and maintenance comprising administering an effective amount of a composition of claim 1.

* * * * *